US012589062B2

(12) United States Patent
Sonoyama

(10) Patent No.: US 12,589,062 B2
(45) Date of Patent: Mar. 31, 2026

(54) POWDERY SOLID COSMETIC PREPARATION

(71) Applicant: Shiseido Company, Ltd., Tokyo (JP)

(72) Inventor: Yuuji Sonoyama, Tokyo (JP)

(73) Assignee: Shiseido Company, Ltd., Tokyo (JP)

( * ) Notice: Subject to any disclaimer, the term of this patent is extended or adjusted under 35 U.S.C. 154(b) by 635 days.

(21) Appl. No.: 17/788,215

(22) PCT Filed: Dec. 18, 2020

(86) PCT No.: PCT/JP2020/047452
§ 371 (c)(1),
(2) Date: Jun. 22, 2022

(87) PCT Pub. No.: WO2021/132082
PCT Pub. Date: Jul. 1, 2021

(65) Prior Publication Data
US 2023/0049630 A1     Feb. 16, 2023

(30) Foreign Application Priority Data

Dec. 23, 2019     (JP) ................................. 2019-232122

(51) Int. Cl.
| | |
|---|---|
| *A61K 8/25* | (2006.01) |
| *A61K 8/02* | (2006.01) |
| *A61K 8/19* | (2006.01) |
| *A61K 8/60* | (2006.01) |
| *A61K 8/891* | (2006.01) |
| *A61K 8/895* | (2006.01) |
| *A61Q 1/12* | (2006.01) |

(52) U.S. Cl.
CPC ................ *A61K 8/25* (2013.01); *A61K 8/022* (2013.01); *A61K 8/19* (2013.01); *A61K 8/60* (2013.01); *A61K 8/891* (2013.01); *A61K 8/895* (2013.01); *A61Q 1/12* (2013.01); *A61K 2800/546* (2013.01)

(58) Field of Classification Search
CPC .......... A61K 8/25; A61Q 19/00; A61Q 17/04; A61Q 1/02; A61Q 1/12; A61Q 15/00; A61Q 17/02
See application file for complete search history.

(56) References Cited

U.S. PATENT DOCUMENTS

| | | | | |
|---|---|---|---|---|
| 2010/0247914 A1* | 9/2010 | Enomoto | ................. | A61K 8/25 |
| | | | | 428/402 |
| 2012/0172440 A1 | 7/2012 | Li et al. | | |

FOREIGN PATENT DOCUMENTS

| | | |
|---|---|---|
| EP | 1 329 485 A1 | 7/2003 |
| EP | 2 233 126 A1 | 9/2010 |
| JP | 2010-235485 A | 10/2010 |
| JP | 2013-227282 A | 11/2013 |
| JP | 2014-094878 A | 5/2014 |
| JP | 2018-177640 A | 11/2018 |
| WO | WO-2010/002262 A1 | 1/2010 |
| WO | WO-2014/207715 A2 | 12/2014 |

OTHER PUBLICATIONS

Machine translation of Tsukiyama, et al., JP-2013227282-A [online]. Espacenet [retrieved on Nov. 27, 2024]. Retrieved from the internet: <https://worldwide.espacenet.com/patent/>. (Year: 2013).*
Machine translation of Table 1, Tsukiyama, et al., JP-2013227282-A [online]. Google Translate [retrieved on Dec. 4, 2024]. (Year: 2013).*

* cited by examiner

*Primary Examiner* — Audrea B Coniglio
(74) *Attorney, Agent, or Firm* — Foley & Lardner LLP

(57) ABSTRACT

An objective of the invention is to provide a powdered solid cosmetic that has excellent powder dispersibility and high impact resistance, while also having a texture similar to that in the case in which an elastic spherical powder is blended. The powdered solid cosmetic according to the present invention contains (A) a non-elastic spherical powder having a crushing strength per particle of 30 MPa or higher; (B) 1% to 15% by mass of iron oxide; (C) a gel-type partially crosslinked organopolysiloxane polymer; and (D) a nonionic surfactant having an HLB of 10 or lower; wherein the (A) non-elastic spherical powder constitutes 90% by mass or more of all spherical powders contained in the cosmetic.

5 Claims, No Drawings

POWDERY SOLID COSMETIC PREPARATION

CROSS-REFERENCE TO RELATED APPLICATIONS

This application is the U.S. National Stage of PCT/ JP2020/047452, filed Dec. 18, 2020, which claims priority to JP 2019-232122, filed Dec. 23, 2019.

TECHNICAL FIELD

The present invention relates to a powdered solid cosmetic. More specifically, the present invention relates to a powdered solid cosmetic that can achieve an excellent texture even while being substantially free of elastic spherical powders, that also has excellent powder dispersibility and provides high impact resistance.

BACKGROUND ART

Powdered solid cosmetics are cosmetic bases that are commonly used in foundations, eyeshadows and the like. Generally, powdered solid cosmetics are composed of a powder that is a main component and an oil that functions as a binder or adhesive thereof. The powder portion is the principal base of the cosmetic and therefore has a significant impact on the texture, such as the spreadability on the skin, the smoothness and the evenness of finish. In particular, spherical powders serve an important role by rolling over the skin, thereby increasing the silkiness, improving the spreadability and achieving a light finish.

As spherical powders, synthetic resins such as polymethyl methacrylate (PMMA), nylon and urethane are often used, particularly in order to improve the smoothness and softness to the touch.

However, among these powders, elastic spherical powders, which have relatively high flexibility, are spherical and therefore have small contact surfaces with other powders, and their elasticity makes them difficult to solidify, so that they have poor moldability. For this reason, even if they can provide powdered solid cosmetics with an excellent texture, it is difficult to achieve sufficient impact resistance at the same time.

Attempts have also been made to improve the impact resistance of powdered solid cosmetics including elastic spherical powders. For example, using a solid oil powder that has been formed into fine particles by means of a gas evaporation method as a binder (Patent Document 1), blending a spherical polyolefin resin powder (Patent Document 2) and using an opposing rotary blade-type mixing apparatus having a specific structure (Patent Document 3) have been proposed. However, these proposals are limited by requiring the use of specific raw materials or specific apparatuses, and further improvements are sought in connection with impact resistance.

RELATED ART

Patent Documents

Patent Document 1: JP 2005-272427 A
Patent Document 2: JP 2006-169207 A
Patent Document 3: JP 2009-167181 A

SUMMARY OF THE INVENTION

Problem to be Solved by the Invention

The present invention was made in view of the aforementioned circumstances, and an objective of the present invention is to provide a powdered solid cosmetic that has excellent powder dispersibility and high impact resistance, while also having a texture similar to that in the case in which an elastic spherical powder is blended.

Means for Solving the Problem

The present inventors performed diligent research towards solving the above-mentioned problem, as a result of which they discovered that, by blending a prescribed non-elastic spherical powder, iron oxide, a gel-type partially crosslinked organopolysiloxane polymer and a non-ionic surfactant having an HLB of 10 or lower, an excellent texture, dispersibility and impact resistance can be realized at the same time in the powdered solid cosmetic. Thus, the present invention was completed.

That is, the present invention is a powdered solid cosmetic containing:

(A) a non-elastic spherical powder having a crushing strength per particle of 30 MPa or higher;

(B) 1% to 15% by mass of iron oxide;

(C) a gel-type partially crosslinked organopolysiloxane polymer; and (D) a non-ionic surfactant having an HLB of 10 or lower;

wherein the (A) non-elastic spherical powder constitutes 90% by mass or more of all spherical powders contained in the cosmetic.

Generally, it is known that, when a large amount of an (A) non-elastic spherical powder is blended, although the impact resistance increases in comparison with the case in which an elastic spherical powder is blended, the roughness to the touch becomes conspicuous, thereby worsening the texture.

Additionally, when a (C) gel-type partially crosslinked organopolysiloxane polymer, which is a high-viscosity fluid, is added, an improvement in the texture can be expected, but there is a tendency for the powder to aggregate, making it difficult for the powder to be uniformly dispersed. In particular, when a (C) gel-type partially crosslinked organopolysiloxane polymer was used in combination with an elastic spherical powder, there were cases in which uneven filling occurred, such as darker-colored portions and lighter-colored portions being visible in the cosmetic, or the impact resistance was largely reduced. For this reason, it was predicted that powder aggregation could not be avoided even in cases in which a (C) gel-type partially crosslinked organopolysiloxane polymer was used in combination with a non-elastic spherical powder.

However, it was discovered that, by using a powder having a crushing strength per particle of 30 MPa or higher as a non-elastic spherical powder combined with a (C) gel-type partially crosslinked organopolysiloxane polymer, and further adding (D) a non-ionic surfactant having an HLB of 10 or lower, surprisingly, the dispersibility of a powder in which a non-elastic spherical powder contains (B) iron oxide is largely improved, and for this reason, powder aggregation does not occur, and moreover, a texture without a sense of roughness, that is smooth and spreadable, can be realized.

Effects of the Invention

The present invention provides a powdered solid cosmetic that has an adequate texture even without blending in an elastic spherical powder, which has commonly been used in conventional powdered solid cosmetics, and also has excellent properties in terms of uniform dispersibility of the powder and impact resistance.

MODES FOR CARRYING OUT THE INVENTION

The powdered solid cosmetic of the present invention includes (A) a non-elastic spherical powder, (B) iron oxide, (C) a gel-type partially crosslinked organopolysiloxane polymer and (D) a non-ionic surfactant. The invention will be described in detail below.

<(A) Non-Elastic Spherical Powder>

Either an inorganic spherical powder or an organic spherical powder may be used as the (A) non-elastic spherical powder in the present invention, as long as it has a crushing strength per particle of 30 MPa or higher, preferably 35 MPa or higher, and more preferably 40 MPa or higher. The crushing strength per particle in the present invention is a value obtained by using an MCT-211 micro compression testing machine manufactured by Shimadzu Corporation to apply a load force at a uniformly increasing rate to one particle of a sample, and computing the strength at the time the particle is crushed. If the crushing strength is lower than 30 MPa, then the flexibility is too high, making it difficult to provide sufficient molding strength, and the dispersibility of the powder cannot be sufficiently increased.

The average particle size of the (A) non-elastic spherical powder is within the range from 1 to 30 preferably within the range from 3 to 20 μm, and more preferably within the range from 5 to 15 μm. If the average particle size is less than 1 μm, then the smoothness when applying the cosmetic is lost, and if the average particle size exceeds 30 μm, then there tends to be squeakiness or grittiness.

Although the shape of the (A) non-elastic spherical powder must be spherical, there is no need for the shape to be perfectly spherical. For example, the cross-section may be elliptical. The shape should preferably be perfectly spherical for the purposes of obtaining a lighter and favorable feeling to the touch.

The (A) non-elastic spherical powder may, for example, be spherical silica, spherical alumina, spherical titania, spherical calcium carbonate or the like. In particular, spherical silica is preferable for the purposes of texture, and porous silica particles are more preferable. Furthermore, the non-elastic spherical powder may be surface-treated. The surface treatment may, for example, be a silicone compound treatment, a fluorine-modified silicone compound treatment, a fluorine compound treatment, a higher fatty acid treatment, a higher alcohol treatment, a fatty acid ester treatment, a metal soap treatment, an amino acid treatment, an alkyl phosphate treatment or the like.

A commercially available product may be used as the (A) non-elastic spherical powder. Examples include products such as Satinier M-5 (JGC Catalysts and Chemicals Ltd.) and Sunsphere L-51 (AGC Si-Tech Co., Ltd.).

The blended amount of the (A) non-elastic spherical powder in the present invention is 6% to 25% by mass, preferably 8% to 20% by mass, and more preferably 10% to 15% by mass relative to the powdered solid cosmetic overall. If the blended amount is less than 6% by mass, then the texture becomes worse, the powder dispersibility is reduced and there are cases in which aggregation occurs. Additionally, even if more than 25% by mass is blended, a texture, moldability and impact resistance that are commensurate with the blended amount tend not to be obtained.

The (A) non-elastic spherical powder must constitute 90% by mass or more, preferably 95% by mass or more and more preferably 99% by mass or more of all spherical powders included in the cosmetic. If the percentage of the (A) non-elastic spherical powder among the spherical powders overall is less than 90% by mass, then the powder dispersibility is reduced and there are cases in which aggregation occurs.

In this case, the "spherical powders" other than the (A) non-elastic spherical powder that may be included in the powdered solid cosmetic of the present invention include all powders that are elastic and spherical. They may, for example, be silicone elastomer powders, silicone powders, silicone resin-coated silicone elastomer powders, polyamide resin powders (nylon powders), polyethylene powders, polymethyl methacrylate powders, polystyrene powders, styrene-acrylic acid copolymer resin powders, benzoguanamine resin powders, polyurethane resin powders and the like.

For the purposes of moldability and impact resistance, it is preferable to blend no elastic powders, whether spherical or non-spherical, in the powdered solid cosmetic of the present invention.

All of the spherical powders (including those that are elastic and non-elastic) included in the powdered solid cosmetic of the present invention constitute 1% to 30% by mass, more preferably 5% to 25% by mass, and even more preferably 5% to 15% by mass relative to the powdered solid cosmetic overall. If the blended amount of the spherical powder is less than 1% by mass, then a sufficient texture cannot be obtained, and if more than 30% by mass is blended, then the moldability and the impact resistance tend to become worse.

Additionally, the (A) non-elastic spherical powder preferably constitutes 5% by mass or more, more preferably 6% by mass or more, or 7% by mass or more, and particularly preferably 10% by mass or more of all powders included in the cosmetic in order to further improve the texture and the moldability. On the other hand, the (A) non-elastic spherical powder preferably constitutes 30% by mass or less, more preferably 25% by mass or less, and even more preferably 20% by mass or less of all powders included in the cosmetic. Even if the percentage of the (A) non-elastic spherical powder in the powders overall is increased, a texture, moldability and impact resistance that are commensurate with the blended amount tend not to be obtained.

<(B) Iron Oxide>

The (B) iron oxide used in the present invention is a pigment-grade iron oxide such as yellow iron oxide, red iron oxide or black iron oxide, which is widely used in normal cosmetics, or any of the above wherein the surfaces have been hydrophobically treated.

The average particle size of the (B) iron oxide is preferably 100 to 500 nm, among which those in which the average particle size is 200 nm or greater are particularly preferred.

As the hydrophobic treatment agent in the case in which the (B) iron oxide is hydrophobically treated, specific examples include alkyl-modified silicones, alkyl triethoxysilane, alkyl trimethoxysilane, perfluoroalkyl phosphoric acid, (alkyl acrylate/dimethyl silicone) copolymer, dextrin palmitate, triethoxysilylethyl polydimethylsiloxyethylhexyl dimethicone, monomethyl polysiloxane, dimethyl polysiloxane, high-molecular-weight silicone, sodium acryloyldimethyl taurate/methacrylamide lauric acid copolymer and the like.

The blended amount of the (B) iron oxide in the present invention is 1% to 15% by mass and more preferably 1% to 7% by mass relative to the powdered solid cosmetic overall. If the blended amount is less than 1% by mass, then there are no problems in terms of the dispersibility but there are cases in which sufficient cosmetic effects are not obtained, and if the blended amount is 15% by mass or greater, then the dispersibility is lost and and there are cases in which uneven filling occurs.

<(C) Gel-Type Partially Crosslinked Organopolysiloxane Polymer>

Component (C) used in the present invention is obtained by crosslink-bonding organopolysiloxanes to obtain a polymer, then swelling the polymer with a solvent comprising a liquid silicone oil to obtain a gel.

As the partially crosslinked organopolysiloxane polymer constituting component (C), there are, for example, partially crosslinked methyl polysiloxanes such as (dimethicone/vinyl dimethicone) crosspolymer and (dimethicone/phenyl vinyl dimethicone) crosspolymer; partially crosslinked alkyl/polyether-comodified silicones such as (PEG-15/lauryl dimethicone) crosspolymer, (dimethicone/PEG-10/15) crosspolymer and (PEG-15/lauryl polydimethylsiloxyethyl dimethicone) crosspolymer; and partially crosslinked polyglycerin-modified silicones such as (dimethicone/polyglycerin-3) crosspolymer, among which one type or a combination of two or more types may be used. Among the above, (dimethicone/vinyl dimethicone) crosspolymer is particularly preferred.

Specific examples of liquid silicone oils that are solvents constituting component (C) include volatile cyclic silicone-based oils and volatile linear silicone-based oils such as dimethicone, cyclopentasiloxane and methyl trimethicone. Among these, dimethicone is particularly preferred.

The partially crosslinked organopolysiloxane polymer content in component (C) is preferably 10% to 30% by mass, and more preferably 15% to 25% by mass.

A commercially available product may be used as component (C). For example, there are products such as KSG-16 ((dimethicone/vinyl dimethicone) crosspolymer, a mixture with dimethicone 6 cs that is 20% to 30% crosslinked), KSG-19 ((dimethicone/vinyl dimethicone) crosspolymer, a mixture with dimethicone 6 cs that is 10% to 20% crosslinked), KSG-310 ((PEG-15/lauryl dimethicone) crosspolymer, a mixture with liquid paraffin that is 25% to 35% crosslinked), KSG-710 ((dimethicone/polyglycerin-3) crosspolymer, a mixture with dimethyl polysiloxane that is 20% to 30% crosslinked), KSG-18A ((dimethicone/phenyl vinyl dimethicone) crosspolymer, a mixture with diphenyl-siloxyphenyl trimethicone that is 10% to 20% crosslinked), KSG-210 ((dimethicone/PEG-10/15) crosspolymer, a mixture with dimethicone that is 20% to 30% crosslinked) and KSG-360Z ((PEG-15/lauryl polydimethylsiloxyethyl dimethicone) crosspolymer, a mixture with dimethicone that is 30% to 40% crosslinked) (all of the above manufactured by Shin-Etsu Chemical Co., Ltd.).

The blended amount of component (C) in the present invention is 1% to 15% by mass, preferably 2% to 10% by mass and more preferably 3% to 7% by mass relative to the powdered solid cosmetic overall. If the blended amount is less than 1% by mass, then there are cases in which the texture becomes worse, and if more than 15% by mass is blended, then there are cases in which the uniformity at the time of application is lost.

6

(D) Non-Ionic Surfactant Having HLB of 10 or Lower

Component (D) is a non-ionic surfactant having an HLB of 10 or lower. HLB is calculated by Kawakami's equation, which is represented by the following expression:

$$HLB = 7 + 11.7 \cdot \log(MW/MO)$$

(where MW represents the molecular weight of the hydrophilic groups and MO represents the molecular weight of the lipophilic groups). When the HLB exceeds 10, uniform dispersion of the powders becomes difficult. The HLB is preferably within the range 2 to 10, more preferably within the range 3 to 6.

The non-ionic surfactant having an HLB of 10 or lower is not particularly limited as long as it can be used in normal cosmetics, and may, for example, be POE (2) stearyl ether, self-emulsifying propylene glycol monostearate, glyceryl myristate, glyceryl monostearate, self-emulsifying glyceryl monostearate, glyceryl monoisostearate, glyceryl mono-oleate, hexaglyceryl tristearate, decaglyceryl pentastearate, decaglyceryl pentaisostearate, decaglyceryl pentaoleate, sorbitan monostearate, sorbitan tristearate, sorbitan monoisostearate, sorbitan sesquiisostearate, sorbitan mono-oleate, POE (6) sorbitol hexastearate, POE (3) castor oil, PEG (2) monostearate, ethylene glycol monostearate, PEG (2) stearate and the like. In the cosmetic according to the present invention, these non-ionic surfactants may be blended as a single type or as a combination of two or more types.

Examples of the (D) non-ionic surfactant that are commercially available products include Cosmol 182V (sorbitan sesquiisostareate; Nisshin Oillio Group) and Nikkol SS-10V (sorbitan monostearate).

The blended amount of the (D) non-ionic surfactant is 0.01% to 5% by mass relative to the powdered solid cosmetic of the present invention overall. Preferably, the blended amount is 0.1% to 1% by mass. If the blended amount is less than 0.01% by mass, then there are cases in which it becomes difficult to achieve sufficient dispersibility, and if more than 5% by mass is blended, then there are cases in which stickiness occurs in terms of the texture.

<Optional Blended Components>

Aside from the above-mentioned components (A) to (D), components that are normally used in cosmetics may also be blended into the cosmetic of the present invention, within a range not compromising the effects of the present invention.

For example, powder components other than those mentioned above, oil-based components, ultraviolet protectants and the like may be appropriately blended as needed.

The powder components other than those mentioned above are not particularly limited as long as they can be used in general cosmetics. There are, for example, talc, kaolin, sericite, muscovite, phlogopite, synthetic mica, synthetic fluorophlogopite, lepidolite, biotite, sintered talc, sintered sericite, sintered muscovite, sintered phlogopite, vermiculite, magnesium carbonate, calcium carbonate, aluminum silicate, barium silicate, calcium silicate, magnesium silicate, strontium silicate, tungstic acid metal salts, magnesium, silica, zeolite, barium sulfate, sintered calcium sulfate (burnt plaster), calcium phosphate, fluorapatite, hydroxyapatite, ceramic powder, metal soaps (for example, zinc myristate, calcium palmitate and aluminum stearate), photochromic titanium oxide (titanium dioxide obtained by sintering iron oxide), reduced zinc oxide; organic powders (for example, silicone elastomer powders, silicone powders, silicone resin-coated silicone elastomer powders, polyamide resin powders (nylon powders), polyethylene powders, polystyrene powders, styrene-acrylic acid copolymer resin powders, benzoguanamine resin powders, polytetrafluoro-ethylene powders, etc.); inorganic white pigments (for example, titanium dioxide, zinc oxide, etc.); inorganic red pigments (for example, iron titanate, etc.); inorganic yellow pigments (for example, ocher, etc.); inorganic black pigments (for example, low-order titanium oxide, etc.); inorganic violet pigments (for example, mango violet, cobalt violet, etc.); inorganic green pigments (for example, chromium oxide, chromium hydroxide, cobalt titanate, etc.); inorganic blue pigments (for example, ultramarine blue, Prussian blue, etc.); pearlescent pigments (for example, bismuth oxychloride; argentine; titanated mica; iron oxide-coated titanated mica; low-order titanium oxide-coated titanated mica; photochromic titanated mica; pigments using talc, glass, synthetic fluorophlogopite, silica, bismuth oxychloride or the like as the substrate instead of mica; pigments coated with low-order titanium oxide, colored titanium oxide, iron oxide, alumina, silica, zirconia, zinc oxide, cobalt oxide, aluminum or the like instead of using titanium oxide as the coating; and as functional pearlescent pigments, those having the surface of a pearlescent pigment coated with resin particles (JP H11-92688 A), those having the surface of a pearlescent pigment coated with aluminum hydroxide particles (JP 2002-146238 A), those having the surface of a pearlescent pigment coated with zinc oxide particles (JP 2003-261421 A), and those having the surface of a pearlescent pigment coated with barium sulfate particles (JP 2003-61229 A); metal powder pigments (for example, aluminum powder, copper powder, etc.); organic pigments such as zirconium, barium or aluminum lakes (for example, organic pigments such as Red No. 201, Red No. 202, Red No. 204, Red No. 205, Red No. 220, Red No. 226, Red No. 228, Red No. 405, Orange No. 203, Orange No. 204, Yellow No. 205, Yellow No. 401 and Blue No. 404; Red No. 3, Red No. 104, Red No. 106, Red No. 227, Red No. 230, Red No. 401, Red No. 505, Orange No. 205, Yellow No. 4, Yellow No. 5, Yellow No. 202, Yellow No. 203, Green No. 3, Blue No. 1, etc.); natural pigments (for example, chlorophyll, β-carotene, etc.) and the like.

The oil-based components are not particularly limited as long as they can be used in general cosmetics, and include liquid oils/fats, solid oils/fats, waxes, hydrocarbon oils, higher fatty acids, higher alcohols, synthetic ester oils, silicone oils and the like.

In the explanation below, POE is an abbreviation for polyoxyethylene and POP is an abbreviation for polyoxypropylene, and the numbers in parentheses after POE or POP represent the average number of moles of POE groups or POP groups added to said compounds.

Liquid oils/fats include, for example, avocado oil, *camellia* oil, turtle oil, macadamia nut oil, corn oil, mink oil, olive oil, rapeseed oil, egg yolk oil, sesame oil, persic oil, wheat germ oil, sasanqua oil, castor oil, linseed oil, safflower oil, cottonseed oil, *perilla* oil, soybean oil, peanut oil, tea seed oil, Japanese *torreya* seed oil, rice bran oil, *Paulownia fargesii* oil, *Paulownia tomentosa* oil, jojoba oil, germ oil, triglycerin and the like.

Solid oils/fats include, for example, cacao butter, coconut oil, horse oil, hardened coconut oil, palm oil, beef tallow, mutton tallow, hardened beef tallow, palm kernel oil, lard, beef bone fat, *Toxicodendron succedaneum* kernel oil, hardened oil, neatsfoot oil, Japan wax, hardened castor oil and the like.

Waxes include, for example, beeswax, candelilla wax, cotton wax, carnauba wax, bayberry wax, insect wax, spermaceti, montan wax, rice bran wax, lanolin, kapok wax, lanolin acetate, liquid lanolin, sugarcane wax, lanolin fatty acid isopropyl ester, hexyl laurate, reduced lanolin, jojoba wax, hardened lanolin, shellac wax, POE lanolin alcohol ether, POE lanolin alcohol acetate, POE cholesterol ether, lanolin fatty acid polyethylene glycol, POE hydrogenated lanolin alcohol ether and the like.

Hydrocarbon oils include, for example, liquid paraffin, ozokerite, squalane, pristane, paraffin, ceresin, squalene, vaseline, microcrystalline wax and the like.

Higher fatty acids include, for example, lauric acid, myristic acid, palmitic acid, stearic acid, behenic acid, oleic acid, undecylenic acid, tall oil acid, isostearic acid, linolic acid, linoleic acid, eicosapentaenoic acid (EPA), docosahexaenoic acid (DHA) and the like.

Higher alcohols include, for example, linear alcohols (for example, lauryl alcohol, cetyl alcohol, stearyl alcohol, behenyl alcohol, myristyl alcohol, oleyl alcohol, cetostearyl alcohol, etc.), branched alcohols (for example, monostearyl glycerin ether (batyl alcohol), 2-decyl tetradecynol, lanolin alcohol, cholesterol, phytosterol, hexyl dodecanol, isostearyl alcohol, octyl dodecanol, etc.) and the like.

Synthetic ester oils include isopropyl myristate, cetyl octanoate, octyldodecyl myristate, isopropyl palmitate, butyl stearate, hexyl laurate, myristyl myristate, decyl oleate, hexyldecyl dimethyl octanoate, cetyl lactate, myristyl lactate, lanolin acetate, isocetyl stearate, isocetyl isostearate, cholesteryl 12-hydroxystearate, ethylene glycol di ethylhexanoate, dipentaerythritol fatty acid ester, N-alkylglycol monoisostearate, neopentyl glycol dicaprate, diisostearyl malate, glycerin di-2-heptylundecanoate, trimethylolpropane tri-2-ethylhexanoate, trimethylolpropane triisostearate, pentaerythrityl tetra-2-ethylhexanoate, glyceryl tri-2-ethylhexanoate, glyceryl trioctanoate, glyceryl triisopalmitate, cetyl 2-ethylhexanoate, 2-ethylhexyl palmitate, glyceryl trimyristate, glyceride tri-2-heptylundecanoate, castor oil fatty acid methyl ester, oleyl oleate, acetoglyceride, 2-heptylundecyl palmitate, diisobutyl adipate, N-lauroyl-L-glutamic acid 2-octyldodecyl ester, di-2-heptylundecyl adipate, ethyl laurate, di-2-ethylhexyl sebacate, 2-hexyldecyl myristate, 2-hexyldecyl palmitate, 2-hexyldecyl adipate, diisopropyl sebacate, 2-ethylhexyl succinate, triethyl citrate and the like.

Silicone oils include silicone compounds such as dimethyl polysiloxane, methylhydrogen polysiloxane, methyl phenyl polysiloxane, stearoxymethyl polysiloxane, polyether-modified organopolysiloxane, fluoralkyl/polyoxyalkylene-comodified organopolysiloxane, alkyl-modified organopolysiloxane, end-unmodified organopolysiloxane, fluorine-modified organopolysiloxane, amino-modified organopolysiloxane, silicone gels, acrylic silicones, trimethylsiloxysilicic acid, silicone RTV rubber and the like.

As ultraviolet protectants (ultraviolet absorbing agents and/or ultraviolet scattering agents), those that are normally blended into cosmetics may be used.

The ultraviolet absorbing agents are not particularly limited and are exemplified by a wide range of ultraviolet absorbing agents that are generally used in cosmetics. For example, there are benzoic acid-based ultraviolet absorbing agents (for example, para-aminobenzoic acid (hereinafter abbreviated to PABA), PABA monoglycerin ester, N,N-dipropoxy PABA ethyl ester, N,N-diethoxy PABA ethyl ester, N,N-dimethyl PABA ethyl ester, N,N-dimethyl PABA butyl ester, etc.); anthranilic acid-based ultraviolet absorbing agents (for example, homomenthyl-N-acetyl anthranilate, etc.); salicylic acid-based ultraviolet absorbing agents (for example, amyl salicylate, menthyl salicylate, homomenthyl salicylate, octyl salicylate, phenyl salicylate, benzyl salicylate, p-isopropanol phenyl salicylate, etc.); cinnamic acid-based ultraviolet absorbing agents (for example, octyl methoxycinnamate, ethyl-4-isopropyl cinnamate, methyl-2, 5-diisopropyl cinnamate, ethyl-2,4-diisopropyl cinnamate, methyl-2,4-diisopropyl cinnamate, propyl-p-methoxycin-namate, isopropyl-p-methoxycinnamate, isoamyl-p-methoxycinnamate, octyl-p-methoxycinnamate (2-ethyl-hexyl-p-methoxycinnamate), 2-ethoxyethyl-p-methoxycinnamate, cyclohexyl-p-methoxycinnamate, ethyl-α-cyano-β-phenyl cinnamate, 2-ethylhexyl-α-cyano-β-phenyl cinnamate, glyceryl mono-2-ethylhexanoyl-diparamethoxycinnamate, etc.); benzophenone-based ultraviolet absorbing agents (for example, 2,4-dihydroxy-benzophenone, 2,2'-dihydroxy-4-methoxybenzophenone, 2,2'-dihydroxy-4,4'-dimethoxybenzophenone, 2,2',4,4'-tet-rahydroxybenzophenone, 2-hydroxy-4-methoxybenzophe-none, 2-hydroxy-4-methoxy-4'-methylbenzophenone, 2-hy-droxy-4-methoxybenzophenone-5-sulfonic acid salts, 4-phenylbenzophenone, 2-ethylhexyl-4'-phenyl-benzophe-none-2-carboxylate, 2-hydroxy-4-n-octoxybenzophenone, 4-hydroxy-3-carboxybenzophenone, etc.); 3-(4'-methylben-zylidene)-d,l-camphor, 3-benzylidene-d,l-camphor; 2-phe-nyl-5-methylbenzoxazole; 2,2'-hydroxy-5-methylphenyl benzotriazole; 2-(2'-hydroxy-5'-t-octylphenyl) benzotriaz-ole; 2-(2'-hydroxy-5'-methylphenyl benzotriazole; dibenza-lazine; dianisoyl methane; 4-methoxy-4'-t-butyldibenzoyl methane; 5-(3,3-dimethyl-2-norbornylidene)-3-pentane-2-one; dimorpholinopyridazino; 2-ethylhexyl-2-cyano-3,3-di-phenyl acrylate; 2,4-bis-{[4-(2-ethylhexyloxy)-2-hydroxy]-phenyl}-6-(4-methoxyphenyl)-(1,3,5)-triazine and the like.

The ultraviolet scattering agents are not particularly lim-ited. As specific examples, there are microparticulate metal oxides, for example, zinc oxide, titanium oxide, cerium oxide, tungsten oxide and the like.

The ultraviolet scattering agents may be non-surface-treated, or may be treated with various types of hydrophobic surface treatments. As surface treatment agents, it is possible to use those that are generally used in the cosmetic field, for example, silicones such as dimethicone and alkyl-modified silicone, alkoxysilanes such as octyl triethoxysilane, dextrin fatty acid esters such as dextrin palmitate, and fatty acids such as stearic acid.

Additionally, pH adjusters, humectants, thickeners, dis-persants, stabilizers, colorants, preservatives, antioxidants, fragrances and the like may be appropriately blended into the powdered solid cosmetic of the present invention within a range allowing the objectives of the present invention to be achieved.

Although a polyhydric alcohol that is normally blended into cosmetics may be blended into the powdered solid cosmetic of the present invention, there is a tendency for the adherence to be reduced. Thus, in the case in which a polyhydric alcohol is blended, the amount should preferably be limited to 1% by mass or less relative to the powdered solid cosmetic overall, and it is more preferable for none to be blended at all (0% by mass). Representative examples of polyhydric alcohols include dipropylene glycol, 1,3-buty-lene glycol, isopentyldiol, 1,2-pentanediol, 1,2-hexanediol, polyethylene glycol, glycerin, diglycerin, sorbitol, maltitol, raffinose and the like.

<Production Method>

The production method of the powdered solid cosmetic of the present invention is not particularly limited, and known methods may be used. Examples include a "dry preparation method" that involves mixing the powder components and the oil-based components without using a solvent, filling a container with the mixture, and molding the cosmetic, a "wet preparation method" that involves adding the powder components and the oil-based components to a volatile dispersion medium to form a slurry, filling a container with the mixture in a slurry state, then removing the solvent to solidify the cosmetic, and a preparation method that involves forming fine droplets from a slurry by means of a mechanical shear force, drying these fine droplets by blow-ing a dry gas thereon, and normally dry-molding the result-ing dry powder (hereinafter, this preparation method will sometimes be referred to as the "W&D preparation method" for convenience). Details regarding the W&D preparation method are described, for example, in JP 2007-55990 A, etc. Due to the W&D preparation method, further improvements can be expected in terms of the adherence to puffs, smooth-ness, and texture such as the sense of fitting.

The solvent used when preparing the slurry in the dry preparation method or the W&D preparation method, though not particularly limited, may be purified water, a cyclic silicone, a light liquid isoparaffin, a lower alcohol, an ether, LPG, a fluorocarbon, N-methylpyrrolidone, a fluoro-alcohol, a volatile linear silicone or the like. Representative examples of lower alcohols include ethanol, isopropanol and the like. These solvents are used differently, as appropriate, either singly or as a mixture of two or more, in accordance with the properties of the blended components that are used.

As product forms of the powdered solid cosmetic accord-ing to the present invention, the present invention may be provided in any product form that is within the range of powdered cosmetics. Specifically, it may be in a product form such as a foundation, an eyeshadow, a cheek color, a body powder, a perfume powder, a baby powder, a pressed powder, a deodorant powder or a face powder.

EXAMPLES

Although the present invention will be explained in further detail by providing examples below, the present invention is not limited in any way thereby. Where not otherwise noted, the blended amounts are indicated in per-centage by mass relative to the system in which the relevant components are blended. Before specifically explaining each example, the evaluation methods that were employed will be explained.

<Dispersibility>

The presence or absence of aggregation in a prepared powdered solid cosmetic was visually observed.

A: Aggregation was not observed at all.

B: Aggregation was slightly observed.

C: There was extreme aggregation of a level not allowing use.

<Impact Resistance>

A powdered solid cosmetic was set in a compact container for cosmetic products, then dropped onto a metal plate from a height of 50 cm with the cosmetic surface facing down-ward, and the number of drops until breakage occurred was studied. For each cosmetic, the number of drops until being damaged was used to evaluate the impact resistance. Those withstanding seven or more drops were determined as having good impact resistance.

<Texture>

A prepared powdered solid cosmetic was applied to the facial surfaces of ten expert panelists, and the lightness of spreading at the time of application was evaluated.

A: Eight or more of the ten panelists replied that the texture was good.

B: Five or more and fewer than 8 of the ten panelists replied that the texture was good.

C: Fewer than five of the ten panelists replied that the texture was good.

Example 1 and Comparative Examples 1 to 3

The powdered solid cosmetics of Example 1 and Comparative Examples 1 to 3 listed in Table 1 below were prepared by the dry preparation method. Specifically, the powder components and the oil-based components indicated in the formulation in Table 1 were mixed with the other components in a Henschel mixer and crushed in a pulverizer, then a resin inner tray container was filled therewith, and dry press molding was performed by a known method to obtain a powdered solid cosmetic.

The resulting powdered solid cosmetics were evaluated in the above-mentioned categories. The evaluation results are also indicated in Table 1.

On the other hand, in the case in which any of (A) to (D) was absent, poor evaluation results were obtained in one of the categories (Comparative Examples 1 to 3). In particular, in the case in which components corresponding to the (A) non-elastic spherical powder were not included, the dispersibility was insufficient (Comparative Example 3). Thus, it was observed that component (A) also contributes to dispersibility.

Examples 2 to 6 and Comparative Example 4

Powdered solid cosmetics with the formulations listed in Table 2 below were prepared by the W&D preparation method. Specifically, the powder components and the oil-based components indicated by the formulations in Table 2 were mixed with the other components, this mixture was mixed with twice the amount of water in a dispersion mixer, then crushed/powdered/dispersed using a medium agitation mill (sand grinder mill) filled with 2 mmφ zirconia beads. Next, the resulting slurry was dried in the state of fine droplets while blowing a dry gas thereon, using an agitation

TABLE 1

|  |  | Ex 1 | Comp Ex 1 | Comp Ex 2 | Comp Ex 3 |
|---|---|---|---|---|---|
| Talc | | 13.38 | 13.38 | 13.38 | 23.38 |
| Mica | | 40 | 40 | 40 | 40 |
| Pigment-grade titanium dioxide | | 10 | 10 | 10 | 10 |
| Titanium dioxide (ultrafine particles) | | 2.5 | 2.5 | 2.5 | 25 |
| Zinc oxide | | 5 | 5 | 5 | 5 |
| Silicone-treated red iron oxide | | 0.15 | 0.15 | 0.15 | 0.15 |
| Silicone-treated yellow iron oxide | | 1.24 | 1.24 | 1.24 | 1.24 |
| Silicone-treated black iron oxide | | 0.15 | 0.15 | 0.15 | 0.15 |
| Chlorphenesin | | 0.2 | 0.2 | 0.2 | 0.2 |
| Spherical silica (crushing strength = 40.62 MPa) *1 | | 10 | 10 | 10 | — |
| (Ca/Al) borosilicate | | 5 | 5 | 5 | 5 |
| Dimethicone-swollen (dimethicone/vinyl dimethicone) crosspolymer *2 | | 5 | 5 | — | 5 |
| Methyl phenyl polysiloxane | | 1.08 | 1.08 | 1.08 | 1.08 |
| Dimethicone | | 1.2 | 1.6 | 6.2 | 1.2 |
| Glyceryl tri(caprylate/caprate) | | 1.5 | 1.5 | 1.5 | 1.5 |
| Octyl methoxycinnamate | | 3 | 3 | 3 | 3 |
| Sorbitan sesquiisostearate (HLB = approx. 4) *3 | | 0.6 | — | 0.6 | 0.6 |
| Total | | 100 | 100 | 100 | 100 |
| [(A) Non-elastic spherical powder]/ [all spherical powders] (%) | | 100 | 100 | 100 | 0 |
| [(A) Non-elastic spherical powders]/ [all powders] (%) | | 11.4 | 11.4 | 11.4 | — |
| Evaluation | Dispersibility | A | C | A | C |
| | Impact resistance (number of drops) | 7 | 4 | 6 | 10 |
| | Texture | A | B | C | C |

*1 Satinier M5 (JGC Catalysts and Chemicals)
*2 KSG-16 (Shin-etsu Chemical)

*3 Cosmol 182V (Nisshin Oillio Group)

As indicated in Table 1, even in the case in which a (B) iron oxide was blended and a large amount of components corresponding to the (A) non-elastic spherical powder were blended, by including components corresponding to the (C) gel-type partially crosslinked organopolysiloxane polymer and components corresponding to the (D) non-ionic surfactant, evaluation results that were satisfactory regarding all of dispersibility, impact resistance and texture were obtained (Example 1).

drying apparatus (spin flash dryer, manufactured by APV Nordic Anhyro), to obtain a dry powder.

A resin inner tray container was filled with the resulting dry powder, and dry press molding was performed by a known method to obtain a solid powdered cosmetic.

The resulting powdered solid cosmetics were evaluated in the above-mentioned categories. The evaluation results are also indicated in Table 2.

TABLE 2

| | Ex 2 | Ex 3 | Ex 4 | Ex 5 | Ex 6 | Comp Ex 4 |
|---|---|---|---|---|---|---|
| Talc | 13.38 | 13.38 | 13.38 | 13.38 | 17.38 | 13.38 |
| Mica | 40 | 40 | 40 | 40 | 40 | 40 |
| Pigment-grade titanium dioxide | 10 | 10 | 10 | 10 | 10 | 10 |
| Titanium dioxide (ultrafine particles) | 2.5 | 2.5 | 2.5 | 2.5 | 2.5 | 2.5 |
| Zinc oxide | 5 | 5 | 5 | 5 | 5 | 5 |
| Silicone-treated red iron oxide | 0.15 | 0.15 | 0.15 | 0.15 | 0.15 | 0.15 |
| Silicone-treated yellow iron oxide | 1.24 | 1.24 | 1.24 | 1.24 | 1.24 | 1.24 |
| Silicone-treated black iron oxide | 0.15 | 0.15 | 0.15 | 0.15 | 0.15 | 0.15 |
| Chlorphenisin | 0.2 | 0.2 | 0.2 | 0.2 | 0.2 | 0.2 |
| Spherical silica (crushing strength = 40.62 MPa) *1 | 10 | 10 | 10 | 10 | 6 | 10 |
| (Ca/Al) borosilicate | 5 | 5 | 5 | 5 | 5 | 5 |
| Dimethicone-swollen (dimethicone/ vinyl dimethicone) crosspolymer *2 | 5 | — | — | — | 5 | — |
| Diphenylsiloxy phenyl trimethicone-swollen (dimethicone/phenyl vinyl dimethicone) crosspolymer *4 | — | 7.5 | — | — | — | — |
| Dimethicone-swollen (dimethicone/PEG-10/15) crosspolymer *5 | — | — | 5 | — | — | — |
| Dimethicone-swollen (PEG-15/lauryl polydimethylsiloxyethyl dimethicone) crosspolymer *6 | — | — | — | 3.52 | — | — |
| Dextrin palmitate | — | — | — | — | — | 5 |
| Methyl phenyl polysiloxane | 1.08 | 0.71 | 1.08 | 1.3 | 1.08 | 1.08 |
| Dimethicone | 1.2 | 0.8 | 1.2 | 1.44 | 1.2 | 1.2 |
| Glyceryl tri(caprylate/caprate) | 1.5 | 0.99 | 1.5 | 1.8 | 1.5 | 1.5 |
| Octyl methoxycinnamate | 3 | 1.98 | 3 | 3.6 | 3 | 3 |
| Sorbitan sesquiisostearate (HLB = approx. 4) *3 | 0.6 | 0.4 | 0.6 | 0.72 | 0.6 | 0.6 |
| Total | 100 | 100 | 100 | 100 | 100 | 100 |
| [(A) Non-elastic spherical powder]/[all spherical powders] (%) | 100 | 100 | 100 | 100 | 100 | 100 |
| [(A) Non-elastic spherical powders]/[all powders] (%) | 11.4 | 11.4 | 11.4 | 11.4 | 6.8 | 11.4 |
| Evaluation      Dispersibility | A | B | B | B | B | C |
| Impact resistance (number of drops) | 10 | 15 | 12 | 12 | 12 | 5 |
| Texture | A | B | B | B | B | C |

*1 Satinier M5 (JGC Catalysts and Chemicals)
*2 KSG-16 (Shin-etsu Chemical)
*3 Cosmol 182V (Nisshin Oillio Group)
*4 KSG-18A (Shin-etsu Chemical)
*5 KSG-210 (Shin-etsu Chemical)
*6 KSG-360Z (Shin-etsu Chemical)

As indicated in Table 2, by including components corresponding to components (A) to (D), evaluation results that were satisfactory regarding all of dispersibility, impact resistance and texture were obtained (Examples 2 to 6). Among the above, a particularly high dispersibility and good texture were obtained in the case in which a dimethicone-swollen (dimethicone/vinyl dimethicone) crosspolymer was used as component (C) (Example 2). Additionally, particularly strong effects were observed to be obtained in the case in which component (A) constituted 10% by mass or more of the powder overall (Example 2), compared with the case in which the proportion of component (A) in the powder overall was low (Example 6).

On the other hand, when dextrin palmitate, which is widely used as a gelling agent, was blended instead of component (C), the results were insufficient for all of dispersibility, impact resistance and texture (Comparative Example 4).

The invention claimed is:

1. A powdered solid cosmetic containing:
(A) a non-elastic spherical powder having a crushing strength per particle of 30 MPa or higher;
(B) 1% to 15% by mass of iron oxide;
(C) a gel-type partially crosslinked organopolysiloxane polymer; and
(D) a non-ionic surfactant having an HLB of 10 or lower;
wherein the (A) non-elastic spherical powder constitutes 90% by mass or more of all spherical powders contained in the cosmetic, wherein the cosmetic does not comprise an organic spherical powder.

2. The powdered solid cosmetic according to claim 1, wherein the (A) non-elastic spherical powder is selected from among spherical silica, spherical alumina, spherical titania and spherical calcium carbonate.

3. The powdered solid cosmetic according to claim 1, wherein the (C) gel-type partially crosslinked organopolysiloxane polymer is a dimethicone/vinyl dimethicone crosspolymer that has been swollen with a liquid silicone oil.

4. The powdered solid cosmetic according to claim 3, wherein the liquid silicone oil is dimethicone.

5. The powdered solid cosmetic according to claim 1, wherein the (D) non-ionic surfactant having an HLB of 10 or lower constitutes 0.01% to 5% by mass of the overall amount of the cosmetic.

* * * * *